US010832403B2

(12) United States Patent
Van Breugel et al.

(10) Patent No.: US 10,832,403 B2
(45) Date of Patent: Nov. 10, 2020

(54) SYSTEMS, METHODS, AND APPARATUSES FOR GENERATING REGIONS OF INTEREST FROM VOXEL MODE BASED THRESHOLDS (71) Applicants: KONINKLIJKE PHILIPS N.V., Eindhoven (NL); YALE UNIVERSITY, New Haven, CT (US)

(72) Inventors: Johanna Van Breugel, Cambridge, MA (US); Aaron Abajian, Cambridge, MA (US); John Treilhard, Cambridge, MA (US); Susanne Smolka, Cambridge, MA (US); Julius Chapiro, Berlin (DE); James Duncan, Cambridbe, MA (US); MingDe Lin, New Haven, CT (US)

(73) Assignees: KONINKLIJKE PHILIPS N.V., Eindhoven (NL); YALE UNIVERSITY, New Haven, CT (US)

( * ) Notice: Subject to any disclaimer, the term of this patent is extended or adjusted under 35 U.S.C. 154(b) by 236 days.

(21) Appl. No.: 15/978,904

(22) Filed: May 14, 2018

(65) Prior Publication Data

US 2019/0347788 A1    Nov. 14, 2019

(51) Int. Cl.
G06T 7/00     (2017.01)
G06T 7/11     (2017.01)
G06T 15/08    (2011.01)

(52) U.S. Cl.
CPC .............. *G06T 7/0012* (2013.01); *G06T 7/11* (2017.01); *G06T 15/08* (2013.01); *G06T 2207/30096* (2013.01)

(58) Field of Classification Search
None
See application file for complete search history.

(56) References Cited

U.S. PATENT DOCUMENTS 7,903,853 B2    3/2011    Muradyan
8,848,998 B1    9/2014    Muradyan
(Continued)

FOREIGN PATENT DOCUMENTS

WO    2015067300 A1    5/2015
WO    2015/110946       7/2015
WO    2015/138385       9/2015

OTHER PUBLICATIONS

International Search Report and Written Opinion dated Aug. 20, 2019 for International Application No. PCT/EP2019/061755 filed May 8, 2019.
(Continued)

*Primary Examiner* — Kim Y Vu
*Assistant Examiner* — Molly Delaney (57) ABSTRACT

The described implementations relate to systems, methods, and apparatuses for generating regions of interest (214) from imaging data (212). Specifically, the regions of interest are generated for tracking treatment efficacy in a more consistent and repeatable manner. The regions of interest can be generated from contrast medium and non-contrast medium enhanced scans (102) of a patient. Voxel data derived from the scans can be collected and distributed according to respective intensity values in order to identify mode voxels (116, 118, 120) for particular ranges (128) of intensities. Regions of interest (110, 112, 114) can then be generated for each identified mode voxel, and standard deviations for the regions of interest can be determined. One or more thresholds can be derived from the determined standard deviations in order to further filter the intensity values and identify filtered groups of voxels to be the resulting regions of interest.

17 Claims, 4 Drawing Sheets

(56) References Cited

U.S. PATENT DOCUMENTS

| | | | |
|---|---|---|---|
| 9,095,273 B2 | 8/2015 | Shmatukha | |
| 2002/0186874 A1* | 12/2002 | Price | G01N 15/147 |
| | | | 382/133 |
| 2003/0176780 A1* | 9/2003 | Arnold | G06T 7/0012 |
| | | | 600/407 |
| 2011/0032389 A1* | 2/2011 | Miyawaki | G06T 7/0002 |
| | | | 348/234 |
| 2013/0079626 A1* | 3/2013 | Shmatukha | A61B 6/03 |
| | | | 600/420 |
| 2014/0010448 A1* | 1/2014 | Lischinski | G06T 5/005 |
| | | | 382/167 |
| 2016/0292864 A1 | 10/2016 | Dabbah | |
| 2016/0300359 A1* | 10/2016 | Lachner | G06T 7/0012 |
| 2018/0053299 A1* | 2/2018 | Gholap | G06T 5/007 |

OTHER PUBLICATIONS

Lin, et al: "Quantitative anid Volumetric European Association for the Study of the Liver and Response Evaluation Criteria in Solid Tumors Measurements: Feasibility of a Semi automated Software Method to Assess Tumor Response after Transcatheter Arterial Chemoembolization", Journal 0f Vascular and Interventional Radiology, Elsevier, Amsterdam, NL, [Online] vol. 23, Jan. 1, 2012.

Sahu, et al: "Imaging Biomarkers of Tumor Response in Neuroendocrine Liver Metastases Treated with Transarterial Chemoembolization: Can Enhancing Tumor Burden of the Whole Liver Help Predict Patient Survival?", Radiology, vol. 283, No. 3, Jun. 1, 2017.

Abajian, et al: "Predicting Treatment Response to Intra-arterial Therapies for Hepatocellular Carcinoma with the Use of Supervised Machine Learning-An Artificial Intelligence Concept.", Journal of Vascular and Interventional Radiology : JVIR 06 2018.

Abajian: "Automated 3d Tumor Enhancement Analyses for Patients Undergoing Transa", Jan. 1, 2017 (Jan. 1, 2017).

Sezgin, et al: "Survey over image thresholding techniques and quantitative performance evaluation", Journal of Electronic Imaging, SPIE—International Society for Optical Engineering, US, vol. 13, No. 1, Jan. 1, 2004.

Raju, et al: "Image Segmentation by using Histogram Thresholding", International Journal of Computer Science Engineering and Technology, vol. 2, No. 1, Jan. 1, 2012.

* cited by examiner

SYSTEMS, METHODS, AND APPARATUSES FOR GENERATING REGIONS OF INTEREST FROM VOXEL MODE BASED THRESHOLDS

This invention was made with government support under CA206180 awarded by National Institutes of Health. The government has certain rights in the invention.

TECHNICAL FIELD

The present invention is directed generally to techniques for processing medical images. More particularly, the various implementations set forth herein relate to generating regions of interest from imaging data corresponding to contrast medium enhanced images.

BACKGROUND

Various clinical pathways exist for identifying tumors, cancers, and other diseases affecting tissues of a patient. However, because many steps in providing a diagnosis can be based on manual techniques performed by a clinician, the results of particular techniques can be subjective and therefore vary across clinicians. For instance, a clinician may be tasked with manually selecting a region of interest from imaging data generated from a scan of tissue of a patient undergoing particular treatment. Because the selection process can vary across clinicians, some clinicians may report different results from the treatment, since the clinicians may have not consistently selected similar regions of interest. As a result, certain treatments may be inaccurately considered inconsequential by some clinicians, despite the treatments having positive effects on patient outcomes. For instance, chemotherapy is often used to treat tissue cancers, however, the determination of whether a treatment is effective can depend on whether clinicians have consistently identified similar regions of interest before and after therapy. If such regions of tissue are not analyzed consistently, the ability to conclude whether a therapy is effective can become futile.

SUMMARY

Embodiments set forth herein relate to systems, methods, and apparatuses for generating regions of interest from imaging data using mode based threshold values. Generating regions of interest in this way can provide consistency across patient diagnoses and outcomes. Oftentimes when a person is diagnosed with cancer, their disease stage may be beyond the capacity of curative treatments. At such times, such as when a patient is diagnosed with liver cancer, the patient may be advised to undergo intra-arterial based therapies (i.e., transcatheter arterial chemoembolization ("TACE")) in order to contain the disease from further progression. When undergoing TACE treatments, a treating physician may need to determine difference between baseline and follow-up images in order to gauge the efficacy of the treatment. However, the efficacy of treatment may not be exhibited simply through tumor size measurements, but may require the analysis of enhancement changes, such as the response of organ and tumor tissues to contrast agents. For instance, a three-dimensional (3D) enhancement-based approach, such as qEASL, can be used to compare changes in tissue.

When using a qEASL approach, a clinician may be required to manual select a region of interest corresponding to healthy tissue. The accuracy of such selections can be different per clinician, thereby leading to variability between selections, limitations in reproducibility, and misclassification of patients as being responsive or unresponsive to therapy. However, the implementations provided herein are set forth as reproducible techniques for accurately selecting regions of interest during routine clinical workflows. Specifically, the implementations set forth herein relate to systems, methods, and apparatuses, for providing automated cut off values for assessing target tissue qualities based on mode intensities exhibited by the target tissues.

In some implementations, an automated process for assessing mode intensities of tissue is set forth. The process can include initially retrieving segments of image data corresponding to 3D multi-phasic contrast enhanced imaging such as CT, MR, CBCT, and/or any other tissue imaging technique. The image data can be processed to identify atrial phase contrast-enhanced image data, and pre-contrast image data, in order that the contrast-enhanced image data can be subtracted from the pre-contrast image data. Using the image data resulting from the subtraction, an intensity histogram for all voxels of image data within a segment of image data can be generated. The voxels can be grouped into N bins, where "N" is any whole number (e.g., a number greater than or equal to 10, 100, 1000, or any other suitable bin number), and a bin with a highest number of voxels can represent a mode bucket.

The process can proceed with regions of interest being generated for each voxel corresponding to the designated mode bucket. A region of interest can be a portion of image data that defines a volume surrounding one or more voxels, such as a voxel in a designated mode bucket. A shape of the region of interest can be, but is not limited to, a cube, a prism, a polygon, a sphere, an oval, and/or any other shape of voxels that can define a volume. Voxels corresponding to each region of interest can then be processed to generate other histograms, such as intensity histograms, and other statistical data, such as a standard deviation for each region of interest. The statistical data can be used to derive collective features such as minimum standard deviation, maximum standard deviation, mean standard deviation, median standard deviation, and/or any other property that can be derived from a collection of data. Any one of the collective features can be used to provide a cutoff value for enhancement and/or non-enhancement of the image data. In some implementations, other cutoff values can be generated using equations such as: 1.) mode+2*minimum standard deviation, 2.) mode+2*maximum standard deviation, 3.) mode+2*mean standard deviation, 4.) mode+2*median standard deviation. Based on the cutoff value and/or the intensity of each voxel, certain variables can be calculated such as, but not limited to, the percentage of enhancing tumor tissue, the volume of enhancing tumor tissue, and/or any other variable that can be useful for identifying affected tissue. Specifically, the mode value can be used to identify areas of tissue characteristic of parenchyma, and other values corresponding to a particular mode value can be used to further characterize the identified areas.

In some implementations, a method implemented by one or more processors is set forth as including operations such as receiving imaging data corresponding to three-dimensional scans of organ tissue. The imaging data can be based on a comparison between one or more contrast medium enhanced scans of a patient and one or more non-contrast medium enhanced scans of the patient. The operations can further include processing voxels of the imaging data to identify one or more modes from the imaging data. The one or more modes can be identified from one or more distributions of enhancement values of the voxels over ranges of enhancement values. The method can further include generating a region of interest for a mode voxel corresponding to the determined one or more modes. The region of interest can identify a volume of data corresponding to a region surrounding the mode voxel. The method can also include generating a tissue threshold value for the enhancement values based on standard deviations of the enhancement values for particular voxels within the region of interest, and identifying a group voxels corresponding to threshold enhancement values that satisfy the tissue threshold value.

In some implementations, the comparison between the one or more contrast medium enhanced scans of a patient and the one or more non-contrast medium enhanced scans can correspond to a subtraction of non-contrast medium enhanced scans from contrast medium enhanced scan data. Processing the voxels of the imaging data can include identifying a first mode corresponding to a first distribution of enhancement values and a second mode corresponding to a second group of enhancement values that are different than the first distribution of enhancement values. Generating the tissue threshold can include arranging the standard deviations according to an absolute value of each standard deviation of the standard deviations and designating a range of the arranged standard deviations as corresponding to healthy organ tissue. In some implementations, generating the tissue threshold value for the enhancement values can be further based on a mean, medium, or mode of the standard deviations of the enhancement values for the particular voxels within the region of interest. The ranges of enhancement values can correspond to bins and processing the voxels of the imaging data to identify the one or more modes from the imaging data includes assigning the voxels to the bins. The mode voxel can correspond to a bin of the bins having a largest number of assigned voxels for a particular distribution of enhancement values.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

The term "controller" is used herein generally to describe various apparatus relating to the implementations discussed herein. A controller can be implemented in numerous ways (e.g., such as with dedicated hardware) to perform various functions discussed herein. A "processor" is one example of a controller which employs one or more microprocessors that may be programmed using software (e.g., microcode) to perform various functions discussed herein. A controller may be implemented with or without employing a processor, and also may be implemented as a combination of dedicated hardware to perform some functions and a processor (e.g., one or more programmed microprocessors and associated circuitry) to perform other functions. Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media (generically referred to herein as "memory," e.g., volatile and non-volatile computer memory such as RAM, PROM, EPROM, and EEPROM, floppy disks, compact disks, optical disks, magnetic tape, etc.). In some implementations, the storage media may be encoded with one or more programs that, when executed on one or more processors and/or controllers, perform at least some of the functions discussed herein. Various storage media may be fixed within a processor or controller or may be transportable, such that the one or more programs stored thereon can be loaded into a processor or controller so as to implement various aspects of the present invention discussed herein. The terms "program" or "computer program" are used herein in a generic sense to refer to any type of computer code (e.g., software or microcode) that can be employed to program one or more processors or controllers.

The term "addressable" is used herein to refer to a device that is configured to receive information (e.g., data) intended for multiple devices, including itself, and to selectively respond to particular information intended for it. The term "addressable" often is used in connection with a networked environment (or a "network," discussed further below), in which multiple devices are coupled together via some communications medium or media.

In one network implementation, one or more devices coupled to a network may serve as a controller for one or more other devices coupled to the network (e.g., in a master/slave relationship). In another implementation, a networked environment may include one or more dedicated controllers that are configured to control one or more of the devices coupled to the network. Generally, multiple devices coupled to the network each may have access to data that is present on the communications medium or media; however, a given device may be "addressable" in that it is configured to selectively exchange data with (i.e., receive data from and/or transmit data to) the network, based, for example, on one or more particular identifiers (e.g., "addresses") assigned to it.

The term "network" as used herein refers to any interconnection of two or more devices (including controllers or processors) that facilitates the transport of information (e.g., for device control, data storage, data exchange, etc.) between any two or more devices and/or among multiple devices coupled to the network. As should be readily appreciated, various implementations of networks suitable for interconnecting multiple devices may include any of a variety of network topologies and employ any of a variety of communication protocols. Additionally, in various networks according to the present disclosure, any one connection between two devices may represent a dedicated connection between the two systems, or alternatively a non-dedicated connection. In addition to carrying information intended for the two devices, such a non-dedicated connection may carry information not necessarily intended for either of the two devices (e.g., an open network connection). Furthermore, it should be readily appreciated that various networks of devices as discussed herein may employ one or more wireless, wire/cable, and/or fiber optic links to facilitate information transport throughout the network.

The term "user interface" as used herein refers to an interface between a human user or operator and one or more devices that enables communication between the user and the device(s). Examples of user interfaces that may be employed in various implementations of the present disclosure include, but are not limited to, switches, potentiometers, buttons, dials, sliders, a mouse, keyboard, keypad, various types of game controllers (e.g., joysticks), track balls, display screens, various types of graphical user interfaces (GUIs), touch screens, microphones and other types of sensors that may receive some form of human-generated stimulus and generate a signal in response thereto.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION

Figure 1:
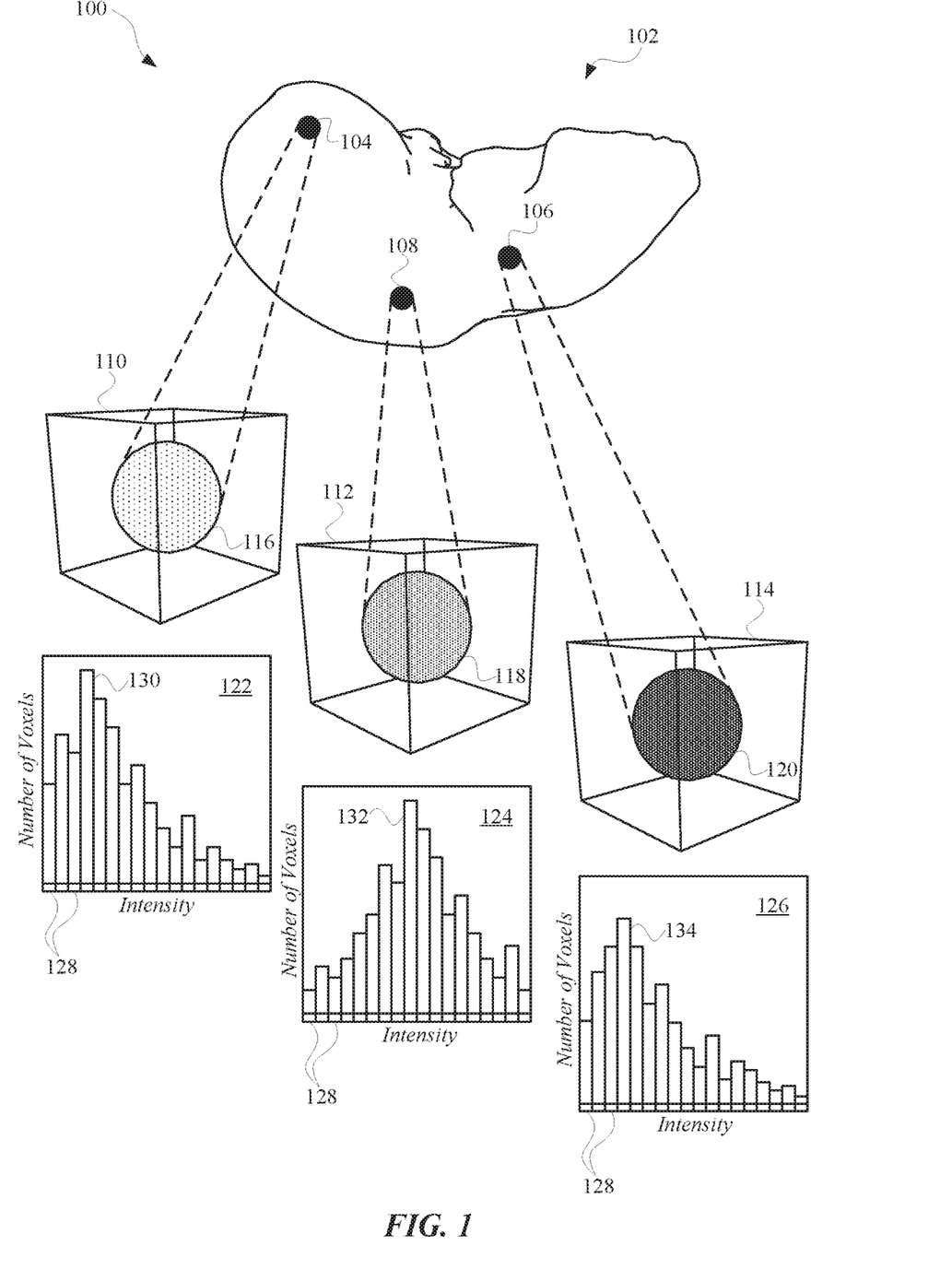
FIG. 1 illustrates a diagram of particular regions of interest generated from imaging data that is based on one or more scans of a patient.

FIG. 1 illustrates a diagram 100 of particular regions of interest generated from imaging data that is based on one or more scans 102 of a patient. The imaging data can characterize a volume or area of a patient (e.g., a liver) that has undergone one or more scanning procedures, such as MRI, CT, ultrasound, and/or any other imaging technique that can be used to scan a body of a person. For instance, a patient can undergo scanning before they receive a particular treatment, and after the patient has received the treatment. In this way, images captured before and after the scans can be compared in order to determine the efficacy of the treatment. Some scanning techniques can involve multiple phases before and after treatment. For instance, a patient can be scanning before being injected with a contrast medium and after being injected with a contrast medium in order to generate contrast-enhanced and non-contrast enhanced image data. Contrast and non-contrast enhanced images can be generated before and after treatment, in order to enhance certain regions of tissue that are expected to be improved or otherwise affected by the treatment.

In order to adequately determine the efficacy of treatment, a clinician should be able to consistently select similar regions of interest from the imaging data generated from the scans 102 over the course of the treatment. The implementations set forth herein provides processes through which a clinician can realize more consistent selections of regions of interest. For instance, imaging data generated from a scan 102 can includes voxels that can characterize an intensity (i.e., lightness, brightness, color, and/or any other property of an image). The intensities of the voxels can be assigned to bins that represent ranges of intensities for purposes of determining a total number of voxels for each bin. The aforementioned process can result in representative histograms being generated. For instance, based on imaging data from the scan 102, a first histogram 122, a second histogram 124, and a third histogram 126 can be generated. Each histogram can include a range of bins 128, and each bin 128 can correspond to a range of intensities. In some implementations, the imaging data can be generated based on a subtraction of a non-contrast medium enhanced scan from a contrast medium enhanced scan, or a subtraction of a contrast medium enhanced scan from a non-contrast medium enhance scan. As a result, the features of tissues enhanced by the contrast medium can be further illuminated or otherwise emphasized in the imaging data.

When the imaging data has been assigned to the bins of one or more histograms, a mode for each histogram can be identified. A mode can refer to a value or a range of values that most commonly appear in a set of data. For instance, the first histogram 122 can have a first mode 130, the second histogram 124 can have a second mode 132, and the third histogram 126 can have a third mode 134. Each mode can be illustrated by a peak value for "number of voxels" within each histogram. When the mode for one or more ranges of bins is identified, the mode voxels can be identified and used to generate regions of interest. For instance, a first mode voxel 116, a second mode voxel 118, and a third mode voxel 120 can be identified from the first histogram 122, the second histogram 124, and the third histogram 126, respectively. Each mode voxel can correspond an intensity or intensities of voxels within a range of voxels that is most common for that respective range of voxels. Therefore, mode voxels for a respective histogram can have a different intensity from mode voxels of a different histogram, as illustrated by the variations in shading of mode voxels in FIG. 1.

For one or more of the mode voxels for each histogram, a three-dimensional (3D) region of interest can be generated to identify a volume of data surrounding each mode voxel. In some implementations, 3D region of interest can be a cube, prism, polygon, sphere, oval, and/or any other 3D shape of any size that can have one or more sides and define a region around a single point (e.g., a voxel of data). A voxel can refer one or more values represented in a three-dimensional space, such as a three-dimensional matrix, grid, array, and/or any other arrangement of data that represents a three-dimensional space. For instance, a first region of interest 110 can be generated for the first mode voxel 116, a second region of interest 112 can be generated for the second mode voxel 118, and a third region of interest 114 can be generated for the third mode voxel 120.

The values of voxels that are part of, and/or surrounded by, the 3D region of interest can be processed to determine one or more statistical variables, such as a standard deviation, for the values of the voxels. For example, the standard deviation for intensity values for the voxels within each 3D region of interest can be generated. As provided in FIG. 1, a histogram for standard deviations can be generated for each group of voxels within the first region of 110, the second region of interest 112, and the third region of interest 114. Furthermore, each histogram can represent ranges of standard deviations for intensity values within each 3D region of interest, respectively. As a result, each histogram of standard deviations can include a mode, from which a threshold can be based.

In some implementations, the histograms of standard deviations for the 3D regions of interest can be based on one or more equations that include calculations of standard deviations. For instance, each value in the histogram can be a result of one or more of the equations 1) mode+2*minimum standard deviation, 2) mode+2*maximum standard deviation, 3) mode+2*mean standard deviation, and/or 4) mode+2*median standard deviation. Therefore, each bin of the histograms can be defined as a range of resulting values from one of the aforementioned equations.

Figure 2:
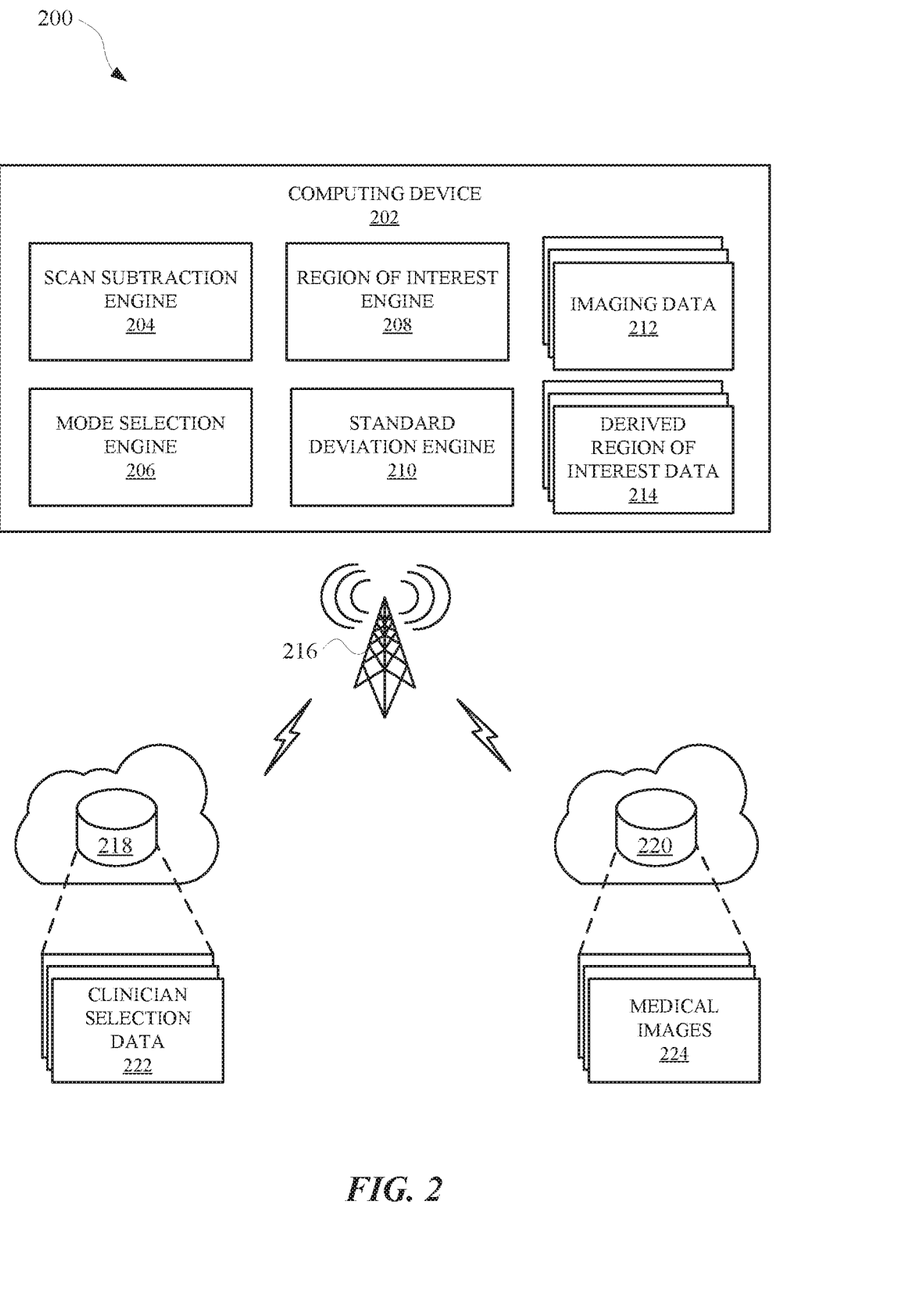
FIG. 2 illustrates a system for generating regions of interest from imaging data in order to provide more consistent monitoring of diseases, treatments, and patients.

FIG. 2 illustrates a system 200 for generating regions of interest from imaging data in order to provide more consistent monitoring of diseases, treatments, and patients. The system 200 can include a computing device 202 for processing imaging data 212 in order to provide derived region of interest data 214 for a clinician or any other user of the computing device 202. The imaging data 212 can be generated based on medical images 224 available at computing device 202, or accessible to the computing device 202 over a network 216 at a remote device 220, such as a server device. The medical images 224 can correspond to one or more scans of a patient. For instance, the medical images 224 can correspond to multi-phase scans in which a patient is scanned prior to being injected with a contrast medium and after being injected with a contrast medium. As a result, scans of a patient that is suffering from a disease such as, for example, liver cancer, will exhibit brighter or more intense features at the diseased area of the liver compared to other areas of tissue of the liver as a result of the contrast medium.

In order to emphasize or isolate areas enhanced by the contrast medium, the computing device 202 can include a scan subtraction engine 204 in order to process imaging data 212 corresponding to multiphase scans. Specifically, the scan subtraction engine 204 can subtract imaging data values, corresponding to pre-contrast medium scans, from imaging data values, corresponding to post-contrast medium scans. As a result, within the imaging data 212, regions of tissue that have absorbed the contrast medium will be further enhanced as a result of the operations of the scanned subtraction engine 204. It should be noted that an engine can refer to one or more applications, scripts, and/or apparatuses capable of performing the operations described with respect to a particular inject. This scan subtraction engine 204 can operate on multiple different slices of multiphase scans of a patient in order to further enhance the imaging data 212.

The computing device 202 can further include a mode selection engine 206. The mode selection engine 206 can operate to arrange voxel data corresponding to the imaging data 212 into different ranges. The voxel data can be assigned to different ranges within a group characterized as a subset of ranges. In this way, each subset of ranges can operate as a histogram or other similar collection of data points, in order to find a mode for each subset of ranges. In other words, each histogram or subset of ranges can include a range that has been assigned the most voxels. Therefore, each voxel within a particular mode can be designated as a mode voxel. The mode selection engine 206 can also operate to identify locations corresponding to the mode voxels. The locations can correspond to three-dimensional coordinates within a space occupied by the voxel data and/or the imaging data 212. For instance, locations of mode voxels can be within a central portion of an organ such as the liver, or along an outer layer of tissue of the organ.

The computing device 202 in further include a region of interest engine 208. The region of interest engine 208 can operate to generate location data corresponding to a region of interest for each of the identified mode voxels, or one or more mode voxels. In some implementations, the region of interest engine 208 can identify voxel data surrounding each identified mode voxel, and a perimeter of the identified voxel data can be characterized as a three-dimensional shape. The three-dimensional shape can be a cube, a prism, a polygon, a sphere, an oval, and/or any other three-dimensional shape that can define a region of interest. Each region of interest generated by the region of interest engine 208 can include one or more points of data of a scan other than the mode voxel. In this way, each region of interest can include some amount of additional data regarding tissue surrounding each mode voxel, respectively.

The data captured by each region of interest can be further processed by a standard deviation engine 210 of the computing device 202. The standard deviation engine 210 can operate to generate standard deviations for enhancement values corresponding to voxels within each region of interest. For each region of interest, the enhancement values may vary, therefore the standard deviations calculated for each region of interest will also vary. However, the standard deviation engine 210 can be tasked with assigning the standard deviations to ranges. As the standard deviations for the regions of interest are assigned, the standard deviations may taper off in the direction that the ranges increase or decrease. The standard deviation engine 210 can then operate to identify a threshold at which, or beyond which, certain voxel data can be removed or otherwise not considered in further processes.

In some implementations, the standard deviation engine 210 can operate to calculate standard deviations as part of a larger equation, the results of which are distributed to corresponding ranges in order to identify a cut-off value for eliminating particular data points. In this way, because certain equations may be more suitable for certain treatments or diseases, the standard deviation engine 210 may swap equations according to the type of scan, the disease being monitored, patient data, the organ or organs being monitored, and/or any other data that can be relevant to a patient. For instance, the computing device 202 can store a table of equations and diseases, types of scans, patient data, organs, and/or any other data in order that the computing device 202 can automatically swap the equations according to the type of imaging data 212 being processed. For example, the standard deviation engine 210 can automatically identify a median standard deviation of the region of interest data based on the received imaging data 212 corresponding to a patient suffering from liver cancer.

The computing device 202 can filter the region of interest data that does not satisfy the identified standard deviation cut-off or threshold in order to generate the derived region of interest data 214. The derived region of interest data 214 can therefore correspond to data that can be consistently derived across different patients. This can allow clinicians to more consistently determine the efficacy of treatments, since many clinicians may otherwise use a different manual process for selecting a region of interest within some amount of imaging data of a patient. The drive region of interest data 214 can be transmitted over the network 216 to a separate remote device 218 and stored as clinician selection data 222. The computing device 202 therefore allows clinicians to share treatment data and/or received data from other clinicians for processing.

Figure 3:
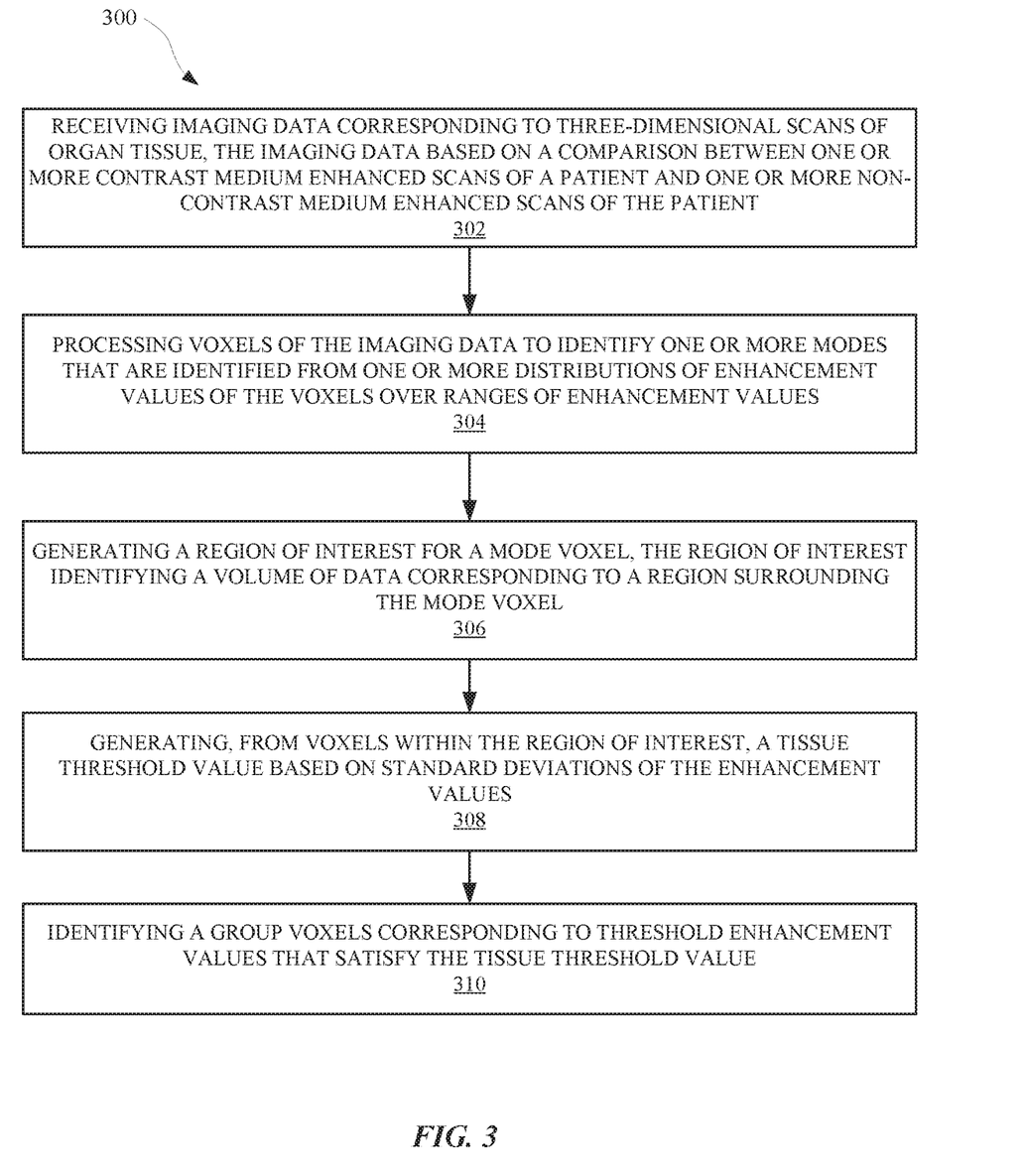
FIG. 3 illustrates a method for identifying voxels of image data corresponding to a region of interest for furthering clinical pathways of particular diseases.

FIG. 3 illustrates a method 300 for identifying voxels of image data corresponding to a region of interest for furthering clinical pathways of particular diseases. The method 300 can be performed by one or more computing devices, applications, and/or any other apparatus or module capable of processing image data. The method 300 can include an operation 302 o receiving imaging data corresponding to three-dimensional scans of organ tissue. The imaging data can be based on a comparison between one or more contrast medium enhanced scans of a patient and/or one or more non-contrast medium enhanced scans of the patient. In some implementations, the imaging data can be derived from scanning techniques such as computed tomography (CT), magnetic resonance imaging (MRI), positron emission tomography (PET), PET-CT, ultrasound, x-ray, endoscopy, elastography, thermography, nuclear medicine functional imaging, SPECT, EEG, MEG, ECG, endocardiography, functional near-infrared spectroscopy, magnetic particle imaging, and/or any other imaging technique that can be used for diagnosing a disease. Furthermore, the imaging data can be based on scans of one or more organs of a patient. For instance, the imaging data can be based on a scan of a liver, therefore the imaging data can characterize multiple different layers of tissue of the liver and any other surrounding tissues.

In some implementations, operation 302 is an optional operation, as some imaging techniques may not require a contrast medium to enhance certain features of a patient. In other implementations, the comparison between one or more contrast medium enhancement scans of a patient and one or more non contrast-enhanced medium scans of the patient can include a subtraction of non-contrast medium enhanced data from contrast medium enhanced data. In this way, portions of tissue that were not enhanced by the contrast medium can be filtered out through the subtraction process in order to emphasize other portions of tissue that were enhanced by the contrast medium.

The method 300 can further include an operation 304 of processing voxels of the imaging data to identify one or more modes that are selected from one or more distributions of enhancement values of the voxels over ranges of enhancement values. The one or more distributions of enhancement values can refer to histograms of enhancement values where the voxels are assigned to bins according to their respective enhancement value. An enhancement value can refer to intensity or lightness designated by a voxel of an image. In some implementations, the enhancement value can refer to an intensity of a voxel relative to the other voxels of the imaging data. When the enhancement values are organized into histograms, a mode for each histogram can be exhibited. The mode can refer to a value or a range of values that are most common within a data set or a larger range of a data set. For instance, multiple histograms can be generated and each histogram of the multiple histograms can correspond to a range of enhancement values. Each histogram can include sub-ranges of enhancement values, and when each enhancement value of each voxel is assigned to a histogram, a mode for each histogram will be exhibited. For instance, a mode for a particular histogram can be a bin or a range of values to which a highest number of voxels have been assigned. Therefore, any voxel assigned to the bin corresponding to the mode can be designated as a mode voxel.

The method 300 can further include an operation 306 of generating a region of interest for a mode voxel. The region of interest can identify a volume of data corresponding to a region surrounding the mode voxel. In other words, the mode voxel can identify a region in space occupied by the organ tissue from which the imaging data was based. The region of interest can be a volume of space that includes the mode voxel, as well as one or more other voxels corresponding to other locations within the space occupied by the organ tissue. In some implementations, the volume of data corresponding to the region of interest can be characterized as a cube, a prism, a sphere, and/or any other shape that can be characterized as a voluminous shape. The operation 306 can optionally include generating multiple regions of interest for multiple mode voxels corresponding to the mode of a particular histogram. Furthermore, the operation 306 can optionally include generating multiple regions of interest for multiple mode voxels of multiple different histograms. The mode voxels for the different histograms can correspond to different ranges of enhancement values. In this way, portions of the imaging data can be more accurately distinguished, thereby leading to layers of tissue being more readily isolated from other layers of tissue, at least with respect to the imaging data.

The method 300 can also include an operation 308 of generating, from voxels within the region of interest, a tissue threshold value based on standard deviations of the enhancement values. The standard deviation can indicate a degree to which each enhancement value for a voxel within a region of interest deviates from the group of voxels within the region of interest as a whole. In some implementations, the tissue threshold value can be based on a minimum, and maximum, a mean, and/or a median standard deviation for enhancement and/or non-enhancement values for voxels within the region of interest. For example, tissue threshold value can be based on the equations such as, but not limited to, 1) mode+2*minimum standard deviation, 2) mode+ 2*maximum standard deviation, 3) mode+2*mean standard deviation, and/or 4) mode+2*median standard deviation.

The method 300 can further include an operation 310 of identifying a group of voxels corresponding to threshold enhancement, or non-enhancement, values that satisfy the tissue threshold value. By basing the tissue threshold value on at least one of the aforementioned equations, voxels that do not satisfy the tissue threshold value can be filtered out in order to provide a more suitable region of interest from which a diagnosis can be based. For example, voxels corresponding to enhancement and/or non-enhancement values that are less than or greater than the tissue threshold value can be filtered out or otherwise not considered part of the group of voxels of a particular region of interest. The resulting region of interest can then be designated as a subject for monitoring, in order that a clinician or other user can track reactions of tissues (e.g., a cancerous tumor) to particular treatments. Furthermore, the aforementioned method and/or operations can promote uniformity for the selected regions of interest across patient populations, thereby leading to better monitoring of treatment outcomes.

Figure 4:
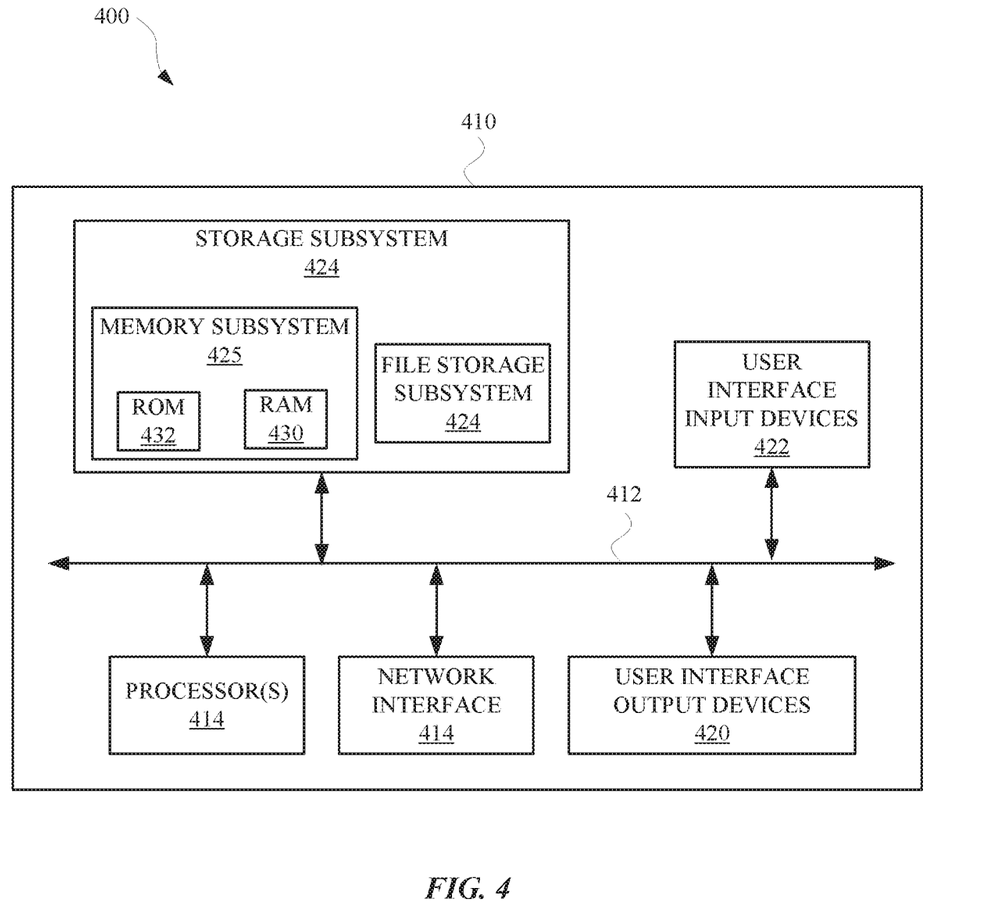
FIG. 4 is a block diagram of an example computer system.

FIG. 4 is a block diagram 400 of an example computer system 410. Computer system 410 typically includes at least one processor 414 which communicates with a number of peripheral devices via bus subsystem 412. These peripheral devices may include a storage subsystem 424, including, for example, a memory 425 and a file storage subsystem 426, user interface output devices 420, user interface input devices 422, and a network interface subsystem 416. The input and output devices allow user interaction with computer system 410. Network interface subsystem 416 provides an interface to outside networks and is coupled to corresponding interface devices in other computer systems.

User interface input devices 422 may include a keyboard, pointing devices such as a mouse, trackball, touchpad, or graphics tablet, a scanner, a touchscreen incorporated into the display, audio input devices such as voice recognition systems, microphones, and/or other types of input devices. In general, use of the term "input device" is intended to include all possible types of devices and ways to input information into computer system 410 or onto a communication network.

User interface output devices 420 may include a display subsystem, a printer, a fax machine, or non-visual displays such as audio output devices. The display subsystem may include a cathode ray tube (CRT), a flat-panel device such as a liquid crystal display (LCD), a projection device, or some other mechanism for creating a visible image. The display subsystem may also provide non-visual display such as via audio output devices. In general, use of the term "output device" is intended to include all possible types of devices and ways to output information from computer system 410 to the user or to another machine or computer system.

Storage subsystem 424 stores programming and data constructs that provide the functionality of some or all of the modules described herein. For example, the storage subsystem 424 may include the logic to perform selected aspects of method 300, and/or to implement one or more of the computing device 202, and/or any other applications, operations, or devices discussed herein.

These software modules are generally executed by processor 414 alone or in combination with other processors. Memory 425 used in the storage subsystem 424 can include a number of memories including a main random access memory (RAM) 430 for storage of instructions and data during program execution and a read only memory (ROM) 432 in which fixed instructions are stored. A file storage subsystem 426 can provide persistent storage for program and data files, and may include a hard disk drive, a floppy disk drive along with associated removable media, a CD-ROM drive, an optical drive, or removable media cartridges. The modules implementing the functionality of certain implementations may be stored by file storage subsystem 426 in the storage subsystem 424, or in other machines accessible by the processor(s) 414.

Bus subsystem 412 provides a mechanism for letting the various components and subsystems of computer system 410 communicate with each other as intended. Although bus subsystem 412 is shown schematically as a single bus, alternative implementations of the bus subsystem may use multiple busses.

Computer system 410 can be of varying types including a workstation, server, computing cluster, blade server, server farm, or any other data processing system or computing device. Due to the ever-changing nature of computers and networks, the description of computer system 410 depicted in FIG. 4 is intended only as a specific example for purposes of illustrating some implementations. Many other configurations of computer system 410 are possible having more or fewer components than the computer system depicted in FIG. 4.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be understood that certain expressions and reference signs used in the claims pursuant to Rule 6.2(b) of the Patent Cooperation Treaty ("PCT") do not limit the scope

What is claimed is:

1. A method implemented by one or more processors, the method comprising:
   receiving imaging data corresponding to three-dimensional scans of organ tissue, the imaging data based on a comparison between one or more contrast medium enhanced scans of a patient and one or more non-contrast medium enhanced scans of the patient;
   processing voxels of the imaging data to identify one or more modes from the imaging data, wherein the one or more modes are identified from one or more distributions of enhancement values of the voxels over ranges of the enhancement values;
   generating a region of interest for a mode voxel corresponding to the determined one or more modes, wherein the region of interest identifies a volume of data corresponding to a region surrounding the mode voxel;
   generating a tissue threshold value for the enhancement values based on standard deviations of the enhancement values for particular voxels within the region of interest by arranging the standard deviations according to an absolute value of each standard deviation of the standard deviations and designating a range of the arranged standard deviations as corresponding to healthy organ tissue; and
   identifying a group of voxels corresponding to threshold enhancement values that satisfy the tissue threshold value.

2. The method of claim 1, wherein the comparison between the one or more contrast medium enhanced scans of the patient and the one or more non-contrast medium enhanced scans corresponds to a subtraction of non-contrast medium enhanced scans from contrast medium enhanced scan data.

3. The method of claim 1, wherein processing the voxels of the imaging data includes identifying a first mode corresponding to a first distribution of enhancement values and a second mode corresponding to a second distribution of enhancement values that are different than the first distribution of enhancement values.

4. The method of claim 1, wherein generating the tissue threshold value for the enhancement values is further based on a mean, medium, or mode of the standard deviations of the enhancement values for the particular voxels within the region of interest.

5. The method of claim 1, wherein the ranges of enhancement values correspond to bins and processing the voxels of the imaging data to identify the one or more modes from the imaging data includes assigning the voxels to the bins.

6. The method of claim 5, wherein the mode voxel corresponds to a bin of the bins having a largest number of assigned voxels for a particular distribution of enhancement values.

7. A non-transitory computer-readable medium configured to store instructions that, when executed by one or more processors, cause the one or more processors to perform operations that include:
   receiving imaging data corresponding to three-dimensional scans organ tissue, the imaging data based on a comparison between one or more contrast medium enhanced scans of a patient and one or more non-contrast medium enhanced scans of the patient;
   processing voxels of the imaging data to identify one or more modes from the imaging data, wherein the one or more modes are identified from one or more distributions of enhancement values of the voxels over ranges the enhancement values;
   generating a region of interest for a mode voxel corresponding to the determined one or more modes, wherein the region of interest identifies a volume of data corresponding to a region surrounding the mode voxel;
   generating a tissue threshold value for the enhancement values based on standard deviations of the enhancement values for particular voxels within the region of interest by arranging the standard deviations according to an absolute value of each standard deviation of the standard deviations and designating a range of the arranged standard deviations as corresponding to healthy organ tissue; and
   identifying a group of voxels corresponding to threshold enhancement values that satisfy the tissue threshold value.

8. The non-transitory computer-readable medium of claim 7, wherein the comparison between the one or more contrast medium enhanced scans of the patient and the one or more non-contrast medium enhanced scans corresponds to a subtraction of non-contrast medium enhanced scans from contrast medium enhanced scan data.

9. The non-transitory computer-readable medium of claim 7, wherein processing the voxels of the imaging data includes identifying a first mode corresponding to a first distribution of enhancement values and a second mode corresponding to a second distribution of enhancement values that are different than the first distribution of enhancement values.

10. The non-transitory computer-readable medium of claim 7, wherein generating the tissue threshold value for the enhancement values is further based on a mean, medium, or mode of the standard deviations of the enhancement values for the particular voxels within the region of interest.

11. The non-transitory computer-readable medium of claim 7, wherein the ranges of enhancement values correspond to bins and processing the voxels of the imaging data to identify the one or more modes from the imaging data includes assigning the voxels to the bins.

12. The non-transitory computer-readable medium of claim 11, wherein the mode voxel corresponds to a bin of the bins having a largest number of assigned voxels for a particular distribution of enhancement values.

13. A system, comprising:
   one or more processors; and
   memory configured to store instructions that, when executed by the one or more processors, cause the one or more processors to perform operations that include:

receiving imaging data corresponding to three-dimensional scans of organ tissue, the imaging data based on a comparison between one or more contrast medium enhanced scans of a patient and one or more non-contrast medium enhanced scans of the patient;

processing voxels of the imaging data to identify one or more modes from the imaging data, wherein the one or more modes are identified from one or more distributions of enhancement values of the voxels over ranges of the enhancement values;

generating a region of interest for a mode voxel corresponding to the determined one or more modes, wherein the region of interest identifies a volume of data corresponding to a region surrounding the mode voxel;

generating a tissue threshold value for the enhancement values based on standard deviations of the enhancement values for particular voxels within the region of interest by arranging the standard deviations according to an absolute value of each standard deviation of the standard deviations and designating a range of the arranged standard deviations as corresponding to healthy organ tissue; and identifying a group of voxels corresponding to threshold enhancement values that satisfy the tissue threshold value.

14. The non-transitory computer-readable medium of claim 13, wherein the comparison between the one or more contrast medium enhanced scans of the patient and the one or more non-contrast medium enhanced scans corresponds to a subtraction of non-contrast medium enhanced scans from contrast medium enhanced scan data.

15. The non-transitory computer-readable medium of claim 13, wherein processing the voxels of the imaging data includes identifying a first mode corresponding to a first distribution of enhancement values and a second mode corresponding to a second distribution of enhancement values that are different than the first distribution of enhancement values.

16. The non-transitory computer-readable medium of claim 13, wherein generating the tissue threshold value for the enhancement values is further based on a mean, medium, or mode of the standard deviations of the enhancement values for the particular voxels within the region of interest.

17. The non-transitory computer-readable medium of claim 13, wherein the ranges of enhancement values correspond to bins and processing the voxels of the imaging data to identify the one or more modes from the imaging data includes assigning the voxels to the bins; and wherein the mode voxel corresponds to a bin of the bins having a largest number of assigned voxels for a particular distribution of enhancement values.

* * * * *